(12) United States Patent
Prasad et al.

(10) Patent No.: US 7,060,678 B2
(45) Date of Patent: Jun. 13, 2006

(54) PEPTIDES COMPRISING FURANOID SUGAR AMINO ACIDS FOR THE TREATMENT OF CANCER

(75) Inventors: Sudhanand Prasad, Ghaziabad (IN); Tushar Kanti Chakraborty, Hyderabad (IN); Archna Mathur, Ghaziabad (IN); Manu Jaggi, Ghaziabad (IN); Ajit Chand Kunwar, Hyderabad (IN); Rama Mukherjee, Ghaziabad (IN); Anand C. Burman, Ghaziabad (IN)

(73) Assignee: Dabur Research Foundation, Ghaziabad (IN)

( * ) Notice: Subject to any disclaimer, the term of this patent is extended or adjusted under 35 U.S.C. 154(b) by 56 days.

(21) Appl. No.: 10/638,107

(22) Filed: Aug. 8, 2003

(65) Prior Publication Data

US 2005/0032707 A1   Feb. 10, 2005

(51) Int. Cl.
*A61K 38/07* (2006.01)
*A61K 38/08* (2006.01)
*C07K 5/02* (2006.01)
*C07K 7/02* (2006.01)
*C07K 9/00* (2006.01)

(52) U.S. Cl. ............................ 514/8; 530/322; 530/332
(58) Field of Classification Search ................ 530/322, 530/328, 329, 330, 332; 514/8, 16, 17, 18
See application file for complete search history.

(56) References Cited

U.S. PATENT DOCUMENTS

| 2003/0050233 A1* | 3/2003 | Burman et al. ................ 514/12 |
| 2003/0105009 A1* | 6/2003 | Prasad et al. .................. 514/12 |
| 2004/0121950 A1* | 6/2004 | Mukherjee et al. ........... 514/12 |

* cited by examiner

*Primary Examiner*—Jeffrey Edwin Russel
(74) *Attorney, Agent, or Firm*—Ladas and Parry LLP (57) ABSTRACT

Anticancer peptides which incorporate furanoid sugar amino acids and compositions made using these peptides are described. Methods for synthesis of the peptides and for preparing the furanoid sugar amino acids are disclosed. The peptides and compositions made using the peptides have pharmacological applications of these peptides especially in the treatment and prevention of cancer and tumors.

24 Claims, 1 Drawing Sheet

FIGURE 1

PEPTIDES COMPRISING FURANOID SUGAR AMINO ACIDS FOR THE TREATMENT OF CANCER

FIELD OF INVENTION

This invention relates to the novel design and synthesis of anticancer peptides by incorporating furanoid sugar amino acids. The invention particularly relates to the synthesis of furanoid sugar amino acids and peptides incorporating furanoid sugar amino acids, which inhibit growth of cancer cells. The invention encompasses methods for generation of these sugar amino acids, peptides containing sugar amino acids, composition containing these peptides and the pharmacological applications of these peptides especially in the treatment and prevention of cancer.

BACKGROUND OF THE INVENTION

The pharmacological limitations of peptides, such as their poor bioavailability or short elimination half-life, are the main reasons for the interest in a rational design of non-peptide mimetics of bioactive peptides. A large variety of modifications of peptide structures have been used for conformationally directed drug design to investigate the active peptide-receptor binding conformation. Of these, constrained peptidomimetics and cyclization of peptides remains of special interest to obtain a distinct bioactive conformation.

Carbohydrates present an attractive option for non-peptide scaffolding. Furanoid sugar amino acids have been used as dipeptide isosteres. They induce turn structures when incorporated in small linear peptides (Chakraborty, T. K. etal; J. Org. Chem. 2000, 65, 6441–6457).

The peptide sequence Leu-Met-Tyr-Pro-Thr-Tyr-Leu-Lys (SEQ ID NO: 1) is reported to be the receptor binding inhibitor of vasoactive intestinal peptide (Said, S. I. & Mutt, V., Ann. N. Y. Acad. Sci., 1, 527,1988). The role of this octapeptide as VIP receptor binding inhibitor has been described in the U.S. Pat. No. 5,217,953. In our U.S. Pat. No. 6,156,725 we have described the anti-cancer role of this VIP receptor binding inhibitor in combination with other neuropeptide analogs. In U.S. patent application Ser. No. 09/248,382, now abandoned, we have described novel analogs of this VIP receptor binding inhibitor incorporating α,α.-dialkylated amino acids and in another U.S. patent application Ser. No. 09/630,345, now U.S. Patent 6,828,304, we have described the lipoconjugates of this octapeptide.

In the present invention we have made peptidomimetic analogs of the mentioned VIP receptor binding inhibitor (SEQ ID NO: 1) replacing the di-/tri-peptides having proline as one of the amino acids, or proline alone, with furanoid sugar amino acids.

Throughout the application the following abbreviations are used with the following meanings:

PyBOP:-Benzotriazole-1-yl-oxy-tris-pyrrolidino-phosphonium hexofluorophospate
DMF: Dimethyl formamide
HBTU:-O-Benzotriazole-N,N,N',N'-tetramethyl-uronium-hexofluoro-phosphate
HOBt:-1-Hydroxy Benzotriazole
DCC:-Dicyclohexyl carbodiimide
DIPCDI:-Diisopropyl carbodiimide
DMAP (4-dimethylamino pyridine)
DIEA:-Diisopropyl ethylamine
DMF:-Dimethyl formamide
DCM:-Dichloromethane
NMP:-N-Methyl-2-pyrrolidinone
TFA: Trifluoroacetic acid
PDC: Pyridinium dichromate
Boc: t-Butyloxy carbonyl
Fmoc: Fluorenyl methoxy carbonyl Throughout the specification and claims, the amino acids residues are designated by their standard abbreviations. Amino acids denote L-configuration unless otherwise indicated by D appearing before the symbol and separated from it by hyphen.

SUMMARY OF THE INVENTION

The present invention relates to peptides containing furanoid sugar amino acids of the following general formula (I)

X-Met-A1-A2-A3-Tyr-Leu-Y and their pharmaceutically acceptable salts wherein,
X is Leu or deleted,
Y is Lys or deleted,
A1 is Tyr or furanoid sugar amino acid
A2 is Pro or furanoid sugar amino acid and
A3 is Thr or furanoid sugar amino acid.

wherein
A1-A2-A3, A1-A2, A2-A3 or A2 is replaced by a furanoid sugar amino acids.

Another way of describing the peptides of this invention is:

X-Met-A1-A2-A3-Tyr-Leu-Y and their pharmaceutically acceptable salts wherein,
X is Leu or deleted
Y is Lys or deleted
A1 is Tyr or a furanoid sugar amino acid, A2 is Pro or a furanoid sugar amino acid and A3 is Thr or a furanoid sugar amino acid wherein at least one of the group A1-A2-A3, A1-A2, A2-A-3 or A2 is replaced by a furanoid sugar amino acid.

The furanoid sugar amino acids are selected from the following:

Saa-1

Saa-2

Where R = H, Bzl or tert-butyl group

Saa-3

Saa-4

The present invention also relates to compositions which are useful for killing or inhibiting the growth and/or multiplication of tumor and/or cancer cells and to the use of the peptides and compositions made using the peptides of this invention for the killing and/or inhibiting the growth and/or multiplication of tumor and/or cancer cells.

The novel compounds of the present invention have important pharmacological applications. They are potent anti-neoplastic agents and thereby possess therapeutic potential in a number of human cancers.

DETAILED DESCRIPTION OF THE INVENTION

The present invention relates to peptides containing furanoid sugar amino acids of the following general formula (I)

X-Met-A1-A2-A3-Tyr-Leu-Y and their pharmaceutically acceptable salts wherein,
X is Leu or deleted,
Y is Lys or deleted,
A1 is Tyr or furanoid sugar amino acid
A2 is Pro or furanoid sugar amino acid and
A3 is Thr or furanoid sugar amino acid.

wherein

A1-A2-A3, A1-A2, A2-A3 or A2 is replaced by a furanoid sugar amino acids.

Another way of describing the peptides of this invention is:

X-Met-A 1-A2-A3-Tyr-Leu-Y and their pharmaceutically acceptable salts wherein,
X is Leu or deleted
Y is Lys or deleted
A1 is Tyr or a furanoid sugar amino acid, A2 is Pro or a furanoid sugar amino acid and
A3 is Thr or a furanoid sugar amino acid wherein at least one of the group A1-A2-A3, A1-A2, A2-A-3 or A2 is replaced by a furanoid sugar amino acid.

The furanoid sugar amino acids can further be either of the following:

Where R = H, Bzl or tert-butyl group

Salts encompassed within the term "pharmaceutically acceptable salts" refer to non-toxic salts of the compounds of this invention. Representative salts and esters include following:

Acetate, ascorbate, benzoate, citrate, oxalate, stearate, trifluoroacetate, succinates, tartarate, lactate, fumarate, gluconate, glutamate, phosphate/diphosphate, valerate. Other salt include Ca, Li, Mg, Na, and K salts; salts of amino acids such as lysine or arginine; guanidine, ammonium, substituted ammonium salts or aluminum salts.

A preferred salt of this invention is a trifluoroacetate salt form.

The salts are prepared by conventional methods.

The peptides obtained after synthesis and purification are in the trifluoroacetate form.

Preferred peptides of this invention are selected from:

| | |
|---|---|
| Leu-Met-Tyr-Saa1-Thr-Tyr-Leu-Lys | (SEQ ID NO: 2) |
| Leu-Met-Tyr-Saa2-Thr-Tyr-Leu-Lys | (SEQ ID NO: 3) |
| Leu-Met-Tyr-Saa3-Thr-Tyr-Leu-Lys | (SEQ ID NO: 4) |
| Leu-Met-Tyr-Saa4-Thr-Tyr-Leu-Lys | (SEQ ID NO: 5) |
| Leu-Met-Saa1-Thr-Tyr-Leu-Lys | (SEQ ID NO: 6) |
| Leu-Met-Saa2-Thr-Tyr-Leu-Lys | (SEQ ID NO: 7) |
| Leu-Met-Saa3-Thr-Tyr-Leu-Lys | (SEQ ID NO: 8) |
| Leu-Met-Saa4-Thr-Tyr-Leu-Lys | (SEQ ID NO: 9) |
| Leu-Met-Tyr-Saa1-Tyr-Leu-Lys | (SEQ ID NO: 10) |
| Leu-Met-Tyr-Saa2-Tyr-Leu-Lys | (SEQ ID NO: 11) |
| Leu-Met-Tyr-Saa3-Tyr-Leu-Lys | (SEQ ID NO: 12) |
| Leu-Met-Tyr-Saa4-Tyr-Leu-Lys | (SEQ ID NO: 13) |
| Met-Saa1-Tyr-Leu | (SEQ ID NO: 14) |
| Met-Saa2-Tyr-Leu | (SEQ ID NO: 15) |
| Met-Saa3-Tyr-Leu | (SEQ ID NO: 16) |
| Met-Saa4-Tyr-Leu | (SEQ ID NO: 17) |
| Leu-Met-Saa1-Tyr-Leu-Lys | (SEQ ID NO: 18) |
| Leu-Met-Saa2-Tyr-Leu-Lys | (SEQ ID NO: 19) |
| Leu-Met-Saa3-Tyr-Leu-Lys | (SEQ ID NO: 20) |
| Leu-Met-Saa4-Tyr-Leu-Lys | (SEQ ID NO: 21) |

The present invention also includes compositions which are useful for killing or inhibiting the growth and/or multiplicaton of tumor and/or cancer cells. The composition may suitably comprise, consist of, or consist essentially of a peptide of this invention which includes a furanoid sugar amino acid. The compositions of this invention can be prepared using a peptide of this invention which includes a furanoid sugar amino acid. In a preferred embodiment, a physiologically effective excipient, carrier, diluent or solvent is used with the peptide to prepare a composition.

The invention also provides a method of treatment for human, mammals or other animals suffering from cancer or other tumors. The method may suitably comprise, consist of, or consist essentially of administering a therapeutically effective dose of the composition so as to inhibit the replication or growth of the tumor or cancer cells and/or to kill, inhibit the growth or inhibit the multiplication of cancer or tumor cells.

Another aspect of the invention provides a method for treating a mammal (including a human being) afflicted with cancer. The methods of this invention comprise, consist essentially or consist of administering to a human or animal, preferably a mammal, a therapeutically effective peptide incorporating a furanoid sugar amino acid or a composition prepared using a peptide of this invention.

The peptides are especially effective in treating cancers of the ovary, colon, larynx, pancreas, oral cavity, liver and endothelial cells.

The methods of this invention comprise, consist of, or consist essentially of administering systematically to the mammal a therapeutically effective amount of a peptide which includes a furanoid sugar amino acid or an effective amount of an active ingredient present in a composition that has been prepared using a peptide described above. An effective dose of the combination or pharmaceutically acceptable salts of the combination ranges from 10 μg/Kg. B. Wt. to 400 μg/Kg. B. Wt of the mammal, with the dose dependent on the effects sought, the manner of administration, and the cancer or tumor being treated. An effective dose means that amount of the peptide or its pharmaceutically acceptable salt or of an active ingredient present in a composition that has been prepared using a peptide described above that will elicit the response that is being sought. In accordance with good clinical practice, it is preferred to administer the composition at a dose that will produce the desired effect without causing undue harmful side effects.

Systemic administration refers to oral, rectal, nasal, transdermal, and parenteral (i.e., intramuscular, intravenous and subcutaneous injections, as well as intrathecal, direct intraventricular, intravenous, intraperitoneal, intranasal or intraocular injections). Other routes of administration include vaginal, transmucosal or intestinal administration.

The peptides have their best in vitro or systemic biological activity (anticancer/antitumor) when their individual concentrations range between $10^{-6}$ M to $10^{-10}$ M (preferably $10^{-8}$ M to $10^{-9}$ M). The stock solution of the peptides prepared for in vitro assays (as described in Example 11) have this concentration.

The compositions may optionally and preferably contain one or more of a pharmaceutically acceptable diluent, excipient, solvent, binder, stabilizer, flavoring, colorant and the like. Such diluents may include buffered saline, isotonic NaCl, Ringer's solution, water, distilled water, polyethylene glycol (neat or in water), Tween in water, dimethylsulfoxide up to 50% in water, propylene glycol (neat or in water), phosphate buffered saline, balanced salt solution, glycerol, and other conventional fluids that are suitable for parenteral administration.

Pharmaceutical compositions, which provide 1 to 20 mg of the peptide, salt thereof or active ingredient which is derived from the peptide, present in the composition per unit dose are preferred and are conventionally prepared as tablets, lozenges, dragees, capsules, powders, aqueous or oily suspensions, syrups, elixirs, time release formulations, sustained release formulations, pills, granules, emulsions, patches, injections, solutions, liposomes and nanoparticle and aqueous solutions. The peptides of this invention or an active ingredient present in a composition that has been prepared using a peptide described above may be administered either alone or as a mixture with other therapeutic agents such as 5-fluorouracil, methotrexate, etoposide, paclitaxel, taxotere, doxorubicin, daunorubicin, vincristine, vinblastine and other such known and established anticancer drugs. Compositions of this invention may be prepared using a peptide of this invention and one or more of another therapeutic agent such as 5-fluorouracil, methotrexate, etoposide, paclitaxel, taxotere, doxorubicin, daunorubicin, vincristine, vinblastine and other such known and established anticancer drugs.

The nature of the pharmaceutical composition employed will, of course, depend on the desired route of administration. The exact formulation, route of administration and dosage will be chosen by the individual physician, clinician or pharmacist based on the patient's condition. Toxicity and therapeutic efficacy of the peptides of this invention can be determined by standard pharmaceutical procedures in cell cultures or experimental animals.

The present invention is further described in detail with reference to the following examples, which are given for the purpose of merely illustrating the invention without limiting it.

Synthesis of Furanoid Sugar Amino Acids

Synthesis of Saa-1

Saa-1 was synthesized from D-fructose in 6 steps as described below.

Step 1

A paste prepared from D-(−)fructose, water (1.2 molar equiv), and $MgCl_2.6H_2O$ (1.0 molar equiv) was added to toluene with stirring at 75° C., followed by stirring for 30 min at the same temperature. Then conc. HCl (8.6 molar equiv) was added to this solution in 5 min and stirred for another 1 h at 75° C. After the solution was cooled to room temperature under continuous stirring, a small amount of water and active charcoal were added and the mixture was stirred again. The organic layer, separated after filtration, was washed with brine, dried over anhydrous $Na_2SO_4$ and concentrated. Purification by column chromatography afforded 5-(chloromethyl)-2-furancarboxaldehyde in 80% yield.

Step 2

The product from step 1 was dissolved in isopropanol free acetone and the solution was cooled to 0° C. Jones' reagent (4.5 molar equiv) was added drop by drop at 0° C. till the colour persisted. The reaction mixture was quenched with isopropanol. Solvents were evaporated under reduced pressure and the residue was extracted with ethyl acetate, washed with 1 M HCl, water, brine, dried ($Na_2SO_4$) and concentrated in vacuo. The crude acid was dissolved in diethyl ether, cooled to 0° C. and $CH_2N_2$ (etheral solution) was added drop by drop till yellow colour persisted. After being stirred for 10 min, ether was removed under reduced pressure. Purification by silica gel column chromatography afforded the methyl ester in 85% yield.

Step 3

The product from step 2 was dissolved in DMF. NaN$_3$ (3.0 molar equiv) was added and the reaction mixture was heated at 65° C. for 1 h. It was then allowed to come to room temperature, quenched with water and extracted with ether. The ether extracts were combined, washed with water, brine, dried (Na$_2$SO$_4$) and concentrated in vacuo. Purification by silica gel column chromatography afforded the intermediate azide, which was directly used in the next step.

Step 4

To the stirred solution of the azide from step 3 in dry methanol, triphenyl phosphine (2.0 molar equiv) was added. After being stirred at room temperature for 2 h, Boc$_2$O (2.0 molar equiv) was added and stirring continued at room temperature for another 30 min, followed by concentration in vacuo. Purification by silica gel column chromatography afforded the N-Boc Saa-1 methyl ester in 80% yield (steps 3 and 4 combined).

Step 5

The product from step 4 was dissolved in THF-MeOH-H$_2$O (3:1:1) and the solution was cooled to 0° C. LiOH.H$_2$O (2.0 molar equiv) was added. After being stirred at room for 1 h, the reaction mixture was acidified with 1M HCl to pH=2, extracted with ethyl acetate, washed with water, brine, dried (Na$_2$SO$_4$) and concentrated in vacuo. Purification by silica gel column chromatography afforded the N-Boc Saa-1 in 90% yield.

Step 6

To a solution of the acid from step 5 in dry CH$_2$Cl$_2$ at 0° C., trifluoroacetic acid (1 mL per 3 mL of CH$_2$Cl$_2$) was added and stirred for 2 h at room temperature. The solution was evaporated to dryness under vacuum in a rotary evaporator and dried thoroughly under high vacuum to give the TFA-salt of Saa-1 in 100% yield.

Synthesis of Saa-2

Saa-2 was synthesized starting from commercially available 3,4-di-O-benzyl-1,2:5,6-diisopropylidene-D-mannitol in 7 steps.

Step 1

Monodeprotection of one of the acetonides of 3,4-di-O-benzyl-1,2:5,6-diisopropylidene-D-mannitol was carried out by treating a solution of the starting material in MeOH with conc. HCl (0.3 molar equiv) drop wise at 0° C. The temperature was then raised to room temperature and stirred for 4 h. It was cooled again to 0° C., neutralized by adding slowly 25% aqueous NH$_3$. MeOH was removed under vacuum. The residue was azeotroped twice with toluene. It was then dissolved in hot CHCl$_3$ and filtered through Celite to remove the precipitated salt. The filtrate and washings were combined and concentrated in vacuo. Purification by silica gel column chromatography gave the required diol in 66% yield.

Step 2

The diol from step 1 was dissolved in CH$_2$Cl$_2$ and the solution was cooled to 0° C. Et$_3$N (2.0 molar equiv) was added, followed by the addition of p-toluenesulfonyl chloride (1.1 molar equiv) and 4-dimethylaminopyridine (DMAP, 0.05 molar equiv). The temperature was then raised to room temperature and stirred for 4 h. It was then diluted with EtOAc, washed with saturated aqueous NH$_4$Cl, brine, dried over anhydrous Na$_2$SO$_4$ and concentrated in vacuo. Purification by silica gel column chromatography gave the required monotosylate in 91% yield.

Step 3

The monotosylate from step 2 was dissolved in dry DMF and sodium azide (NaN$_3$, 2.0 molar equiv) was added to it. The reaction mixture was heated to 80° C. and stirred for 3 h at the same temperature. It was then cooled to room temperature and diluted with EtOAc, washed with water, brine, dried over anhydrous Na$_2$SO$_4$ and concentrated in vacuo. Purification by silica gel column chromatography gave the required azide in 95% yield.

Step 4

To a solution of the azide from step 3 in dry toluene, triphenylphosphine (2.0 molar equiv) was added at room temperature and the reaction mixture was then refluxed for 3 h. It was then cooled to room temperature and Boc$_2$O (2.0 molar equiv) was added. After stirring for 0.5 h, the reaction mixture was diluted with EtOAc (ethyl acetate), washed with water, brine, dried over anhydrous Na$_2$SO$_4$ and concentrated in vacuo. Purification by silica gel column chromatography gave the required N-Boc aziridinyl intermediate in 91% yield.

Step 5

The product from step 4 was dissolved in dry CH$_2$Cl$_2$ and treated with a MeOH solution (CH$_2$Cl$_2$:MeOH=4:1) of (±)-camphorsulfonic acid (1.0 molar equiv) by drop wise addition at 0° C. After 5 min, the reaction mixture was neutralized by adding slowly 25% aqueous NH$_3$. It was then diluted with EtOAc, washed with brine, dried over anhydrous Na$_2$SO$_4$ and concentrated in vacuo. Purification by silica gel column chromatography gave the required N-Boc-6-amino-2,5-anhydro-3,4-di-O-benzyl-6-deoxy-D-mannitol in 95% yield.

Step 6

The product from step 5 was dissolved in dry DMF and cooled to 0° C. Pyridinium dichromate (PDC, 4 molar equiv) was added portion wise and the reaction mixture was stirred at room temperature for 12 h. It was then diluted with EtOAc, washed with saturated aqueous CuSO$_4$, brine, dried over anhydrous Na$_2$SO$_4$ and concentrated in vacuo. Purification by silica gel column chromatography gave the required N-Boc-6-amino-2,5-anhydro-3,4-di-O-benzyl-6-deoxy-D-mannonic acid in 77% yield.

Step 7

To a solution of the acid from step 6 in dry CH$_2$Cl$_2$ at 0° C., trifluoroacetic acid (1 mL per 3 mL of CH$_2$Cl$_2$) was added and stirred for 2 h at room temperature. The solution was evaporated to dryness in a rotary evaporator and dried thoroughly under high vacuum to give the TFA-salt of Saa-2 in 100% yield.

Synthesis of Saa-3

Saa-3 was synthesized from N-Boc Saa-1 methyl ester in 3 steps.

Step 1

The N-Boc Saa-1 methyl ester from step 4 in the synthesis of Saa-1 was dissolved in methanol and hydrogenated on 20% $Pd(OH)_2$—C (50 mg per mmol of the starting material) with stirring at room temperature for 4 h. The catalyst was filtered off through a pad of Celite and the filter cake was washed with MeOH. The filtrate and washings were combined and concentrated under reduced pressure. The residue was chromatographed on silica gel to give N-Boc Saa-2 methyl ester in 95% yield.

Step 2

The product from step 1 was dissolved in THF-MeOH—$H_2O$ (3:1:1) and the solution was cooled to 0° C. $LiOH.H_2O$ (2.0 molar equiv) was added. After being stirred at room for 1 h, the reaction mixture was acidified with 1M HCl to pH=2, extracted with ethyl acetate, washed with water, brine, dried ($Na_2SO_4$) and concentrated in vacuo. Purification by silica gel column chromatography afforded the acid in 90% yield.

Step 3

To a solution of the acid from step 2 in dry $CH_2Cl_2$ at 0° C., trifluoroacetic acid (1 mL per 3 mL of $CH_2Cl_2$) was added and stirred for 2 h at room temperature. The solution was evaporated to dryness under vacuum in a rotary evaporator and dried thoroughly under high vacuum to give the TFA-salt of Saa-3 in 100% yield.

Synthesis of Saa-4

Saa-4 was synthesized from L-glutamic acid in 9 steps.

Step 1

To a solution of L-glutamic acid in water, an aqueous solution of $NaNO_2$ (1.2 molar equiv) and 2N $H_2SO_4$ (1.2 molar eqiv) were added simultaneously drop by drop. After the addition was over, the solution was stirred at room temperature for an additional 15 h. The water was removed in a rotary evaporator under reduced pressure by heating below 50° C. The gummy solid was triturated with 150 mL of boiling acetone and the hot solution was filtered and set aside to cool. This operation is repeated four times. Removal of solvent in a rotary evaporator afforded crude (5S)-5-carboxyl-2-oxo-tetrahydrofuran, which was purified by vacuum distillation to afford pure compound in 66% yield as an oil.

Step 2

The acid function of (5S)-5-carboxyl-2-oxo-tetrahydrofuran was reduced to alcohol by drop-wise addition of $BH_3$-$Me_2S$ (1.1 molar equiv) in tetrahydrofuran (THF) at 0° C. The solution was stirred at room temperature for 12 h. Methanol containing 4.5% triethylamine was added drop wise while cooling. The resulting solution with pH~7–8 was evaporated to dryness, the residue dissolved in MeOH and the solution evaporated again to afford a pale yellow oil which was purified by column chromatography to give the resulting (5S)-5-(hydroxymethyl)-2-oxo-tetrahydrofuran in 78% yield as an oil.

Step 3

The product from step 2 was dissolved in dry $CH_2Cl_2$ and the solution was cooled to 0° C. Triethylamine (1.5 molar equiv) was added. After 10 min, trityl chloride (1.1 molar equiv) followed by DMAP (0.2 molar equiv) were added and stirred over night at room temperature. The reaction was then quenched with saturated $NH_4Cl$ solution, the organic layer was separated and the aqueous layer was extracted with EtOAc. The combined organic extracts were washed with water, brine, dried ($Na_2SO_4$) and concentrated in vacuo. Purification by column chromatography afforded (5S)-5-(trityloxymethyl)-2-oxo-tetrahydrofuran in 76% yield.

Step 4

The product from step 3 was dissolved in $CH_2Cl_2$ and the solution was cooled to −78° C. DIBAL-H (1.2 M in toluene, 1.1 molar equiv) was added drop wise and stirred for 15 min at this temperature. The reaction mixture was then quenched with MeOH followed by saturated sodium potassium tartarate solution and stirred for 1 h. The organic layer was separated and the aqueous layer was extracted with EtOAc. The combined organic extracts were washed with water, brine, dried ($Na_2SO_4$) and concentrated in vacuo. Purification by column chromatography afforded the expected lactol in 86% yield as a mixture of diastereomers at the anomeric position.

Step 5

The lactol from step 4 was dissolved in $CH_2Cl_2$ and the solution was cooled to 0° C. Triethylamine (1.5 molar equiv) was added drop wise. After 10 min, $Ac_2O$ (1.2 molar equiv) was added followed by DMAP (0.2 molar equiv) and stirred for 30 min. The reaction was then quenched with saturated $NH_4Cl$ solution, the organic layer was separated and the aqueous layer was extracted with EtOAc. The combined organic extracts were washed with water, brine, dried ($Na_2SO_4$) and concentrated in vaccuo. Purification by column chromatography afforded the expected acetate in 96% yield as a mixture of diastereomers at the anomeric position.

Step 6

The acetate from step 5 was dissolved in acetonitrile and to it trimethylsilyl cyanide (1.5 molar equiv) was added at room temperature. This was followed by the addition of $BF_3.Et_2O$ (0.8 molar equiv) and the reaction mixture was stirred for 4 h. The solution was then concentrated and purified by column chromatography to afford mixture of glycosyl cyanides in 64% yield. The isomers were separated at this stage by silica gel column chromatography.

Step 7

The (2S,5R)-syn isomer from step 6 was dissolved in dry ether and the solution was cooled to 0° C. $LiAlH_4$ (2.5 molar equiv) was added portion wise. After the addition was over, the solution was refluxed for 3 h. It was then cooled to 0° C. and quenched by the sequential drop wise addition of water (1 mL per g of LiAlH$_4$), 3N NaOH (1 mL per g of LiAlH$_4$) and water (3 mL per g of LiAlH$_4$). Stirring was continued till the free flowing solids were formed. Then the mixture was filtered through a sintered funnel, washed thoroughly with EtOAc. The combined organic filtrate and washings were concentrated under reduced pressure to dryness. The resulting crude amine was dissolved in CH$_2$Cl$_2$ and treated with Boc$_2$O (1.5 molar equiv) at 0° C. and stirred for 1 h at room temperature. Then the solution was concentrated in vacuo and directly subjected to purification by column chromatography to afford (2S,5R)—N-Boc-5-(aminomethyl)-2-(hydroxymethyl)-tetrahydrofuran in 55% yield.

Step 8

The alcohol from step 7 was dissolved in CH$_3$CN and the solution was added at 0° C. to a mixture of NaIO$_4$ (3 molar equiv) and RuCl$_3$.3H$_2$O (0.01 molar equiv) in CH$_3$CN:CCl$_4$: H$_2$O (1:1:1.5) that had been stirred at room temperature for 45 min. After stirring for 5 min, an additional amount of NaIO$_4$ (1.0 molar equiv) was added to the reaction mixture. After 2 h, it was diluted with EtOAc, washed with saturated aqueous NH$_4$Cl, brine, dried (Na$_2$SO$_4$), and concentrated in vacuo. The residue was purified by silica gel column chromatography to furnish the desired acid in 80% yield.

Step 9

To a solution of the acid from step 8 in dry CH$_2$Cl$_2$ at 0° C., trifluoroacetic acid (1 mL per 3 mL of CH$_2$Cl$_2$) was added and stirred for 2 h at room temperature. The solution was evaporated to dryness in a rotary evaporator and dried thoroughly under high vacuum to give the TFA-salt of Saa-4 in 100% yield.

Synthesis of Peptides

The peptide analogs containing sugar amino acids in the present invention have been generated by using solid phase techniques or by a combination of solution phase procedures and solid phase techniques or by fragment condensation. The methods for the chemical synthesis of polypeptides are well known in the art (Stewart and Young, 1969, Solid Phase Peptide Synthesis, W.H. Freeman Co.).

In a preferred embodiment of the present invention the peptides including the sugar amino acids were synthesized using the Fmoc strategy, on a semi automatic peptide synthesizer (CS Bio, Model 536), using optimum side chain protection. The peptides were assembled from C-terminus to N-terminus. Peptide acids at the carboxy-terminus were synthesized using Wang resin. The loading of the first Fmoc protected amino acid was achieved via an ester bond formation with the solid support, mediated by Diisopropylcarbodiimide (DIPCDI) and HOBt. Substitution levels for automated synthesis were preferably between 0.4 and 1.2 mmole amino acid per gram resin.

In a particularly preferred embodiment of the present invention the following chemical moieties were used to protect reactive side chains of the peptides during the synthesis procedure: The N-terminal amino group was protected by 9-fluorenylmethoxycarbonyl (Fmoc) group. The hydroxyl groups of threonine and tyrosine were preferably protected by t-butyl group. Leucine, methionine and proline were used unprotected.

The first coupling with Wang resin was carried out using 4–8 equivalents of Fmoc protected amino acid. DCC/DIPCDI and HOBt were preferably used as activating agents in 4–8 equivalents. DMAP was used in 0.3–1 equivalents to facilitate the first coupling reaction. The furanoid sugar amino acids are coupled during this step.

In a preferred embodiment of the invention, 2–8 equivalents of Fmoc protected amino acid per resin nitrogen equivalent were used. The activating reagents used for coupling amino acids to the resin, in solid phase peptide synthesis, are well known in the art. These include PyBOP, HBTU, HOBt. Preferably, DCC or DIPCDI/HOBt or HBTU/DIEA and PyBOP/DIEA were used as activating reagents in the coupling reactions.

The protected amino acids were either activated in situ or added in the form of preactivated esters known in the art such as N-hydroxy succinamide esters, pentafluorophenyl esters etc. The coupling reaction was carried out in DMF, DCM or NMP or a mixture of these solvents and was monitored by Kaiser test [Kaiser et al., Anal. Biochem., 34, 595–598 (1970)]. In case of a positive Kaiser test, the appropriate amino acid was re-coupled using freshly prepared activated reagents.

After the assembly of the peptide analog was completed, the N-terminal Fmoc group was removed using 20% piperidine in DMF for 30 min. The peptide-resin was washed 2–3 times with DMF, followed by methanol and dried. The gain in weight of the resin because of the added peptide chain was recorded. The side chain protecting groups in the analogs were deprotected and the peptide was simultaneously cleaved from the resin support by treatment with trifluoroacetic acid, crystalline phenol, ethanedithiol, thioanisole and de-ionized water for 1.0 to 4.0 hours at room temperature. The crude peptide was obtained by precipitation with cold dry ether, filtered, dissolved, and lyophilized. The crude peptide was analysed on analytical HPLC system and purified by preparative HPLC on C-18 reverse phase column using a gradient of 0.1% TFA in acetonitrile and water. The eluted fractions were reanalyzed on analytical HPLC system using a C18 reverse-phase column. Acetonitrile was evaporated and the fractions were lyophilized to obtain the pure peptide. The identity of each peptide was confirmed by mass spectrometry.

The present invention will be further described in detail with reference to the following examples, as will be appreciated by a person skilled in the art is merely illustrative and should not be construed as limiting. Various other modifications of the invention will be possible without departing from the spirit and scope of the present invention.

First Loading on Wang Resin

A typical loading of the first Fmoc protected amino acid on Wang Resin, was carried out using 0.5–1.0 g of 4-Hydroxymethylphenoxy Resin 1% DVB cross-linked resin (100–200 mesh), procured from Advanced Chemtech, Louisville, Ky., U.S.A. Swelling of the resin was typically carried out in dichloromethane measuring to volumes 10–40 ml/g resin. The resin was allowed to swell in methylene chloride (2×25 ml, for 10 min.). It was washed once in dimethylformamide (DMF) for 1 min. All solvents in the protocol were added in 20 ml portions per cycle. For loading of the first amino acid on hydroxyl group of the resin, the first amino acid, was weighed in 2–8 fold excess, along with a similar fold excess of HOBt, in the amino acid vessel of the peptide synthesizer. These were dissolved in DMF and activated with DIPCDI and 4-dimethyl amino pyridine just prior to the addition to the resin in the reaction vessel of the peptide synthesizer. The coupling reaction was allowed to proceed for 2–24 hrs. The resin was subsequently washed, dried, and weighed. The loading of the amino acid on the resin was confirmed by the weight gain of the resin. If the gain in weight was as expected, capping of the unreacted sites on the resin was carried out with 10% acetic anhydride, 10% DIEA and 80% DMF for 30 min. If the gain in weight was less than expected, re-coupling was carried out. The washing steps after the coupling reaction was followed by deprotection of the Fmoc group of the attached amino acid using 20% piperidine in DMF for 30 min.

EXAMPLE 1

Synthesis of Leu-Met-Tvr-Saa2-Thr-Tyr-Leu-Lys (SEQ ID NO: 3)

The synthesis of the peptide (SEQ ID NO: 3) was initiated by loading the amino acid Fmoc-Lys-OH on Wang resin (Substitution=1.2 mM/g) on 0.6 mM scale of synthesis. It was subjected to stepwise deprotection and coupling steps in the synthesis cycle. In each coupling reaction, a three to five fold excess of appropriate Fmoc amino acid, HBTU and DIEA were used. The average coupling time for each amino acid was between 0.5–3 hrs. On completion of synthesis, the N-terminal Fmoc protecting group was removed to give 0.136 g of the peptide-loaded resin. This was subjected to cleavage in a cleavage mixture consisting of trifluoroacetic acid and scavengers, crystalline phenol, thioanisole, ethanedithol and water for a period of 1.5 to 5.0 hours at room temperature with continuous stirring. The peptide was precipitated using cold dry ether to obtain 600 mg of the crude peptide. The crude peptide was analysed on a C18 analytical reverse phase HPLC column (250×4) on a gradient system comprising of acetonitrile and water in 0.1% TFA as described previously. The sugar amino acid, Saa2 (with R=OBzl) was used in the peptide sequence (SEQ ID NO.: 3) and one prominent peak was obtained on HPLC. The peptide peak was purified on a preparative HPLC system using C18 reverse phase semi-preparative column (250×10) using a gradient of 0.1% TFA in acetonitrile and water. The collected fractions were re-analysed on analytical HPLC and lyophilized.

EXAMPLE 2

Synthesis of Leu-Met-Saa3-Thr-Tyr-Leu-Lys (SEQ ID NO: 8)

The synthesis of this peptide was initiated by loading the amino acid Fmoc-Lys-OH on Wang resin (Substitution=1.2 mM/g) on 0.3 mM scale of synthesis. It was subjected to stepwise deprotection and coupling steps in the synthesis cycle. In each coupling reaction, a three to five fold excess of appropriate Fmoc amino acid, HBTU and DIEA were used. The average coupling time for each amino acid was between 1–5 hrs. On completion of synthesis, the N-terminal Fmoc protecting group was removed to give 0.585 g of the peptide-loaded resin. This was subjected to cleavage in a cleavage mixture consisting of trifluoroacetic acid and scavengers, crystalline phenol, thioanisole, ethanedithol and water for a period of 1.5 to 5.0 hours at room temperature with continuous stirring. The peptide was precipitated using cold dry ether to obtain 280 mg of the crude peptide. The crude peptide was analysed on a C, 18 analytical reverse phase HPLC column (250×4) on a gradient system comprising of acetonitrile and water in 0.1% TFA as described previously. The sugar amino acid, Saa3, used in the peptide sequence was racemic in nature and the peptide was resolved into two enantiomers, as two prominent peaks on HPLC. The individual peaks were purified and collected on a preparative HPLC system using C18 reverse phase semi-preparative column (250×10) using a gradient of 0.1% TFA in acetonitrile and water. The collected fractions were re-analysed on analytical HPLC and lyophilized. The two pure enantiomers was sent for MALDI mass spectrometer analysis. The observed molecular weight and calculated molecular weight were in agreement for the two peptide enantiomers (calculated mass=895; observed mass=896.5 and 896.4 respectively).

EXAMPLE 3

Synthesis of Leu-Met-Saa4-Thr-Tyr-Leu-Lys (SEQ ID NO: 9)

The synthesis of the peptide (SEQ ID NO: 9) was carried out on Wang resin (Substitution=1.2 mM/g) on 0.3 mM scale of synthesis as in the examples above to give 0.620 g of the peptide-loaded resin, post-deprotection of the N-terminal Fmoc group. This was subjected to cleavage in a cleavage mixture consisting of trifluoroacetic acid and scavengers, crystalline phenol, thioanisole, ethanedithol and water for a period of 1.5 to 5.0 hours at room temperature with continuous stirring. The peptide was precipitated using cold dry ether to obtain 264 mg of the crude peptide, obtained as a single prominent peak on RP-HPLC. The crude peptide was purified on C-18 HPLC column as above and the collected fractions were analysed on analytical HPLC and lyophilized. The HPLC pure peak was sent for MALDI mass spectrometer analysis. The observed molecular weight and calculated molecular weight were in agreement (calculated mass=895; observed mass ($M+K^+$=933.5).

EXAMPLE 4

Synthesis of Leu-Met-Tvr-Saa3-Thr-Tyr-Leu-Lys (SEQ ID NO: 12)

The synthesis of peptide (SEQ ID NO: 12) was carried out on 0.3 mM scale of synthesis, on Wang resin (1.2 mM/g), in a manner similar to that described in Example 2 above, to give 0.563 g of the peptide loaded resin. Cleavage of the peptide from the resin was carried out in a cleavage mixture consisting of trifluoroacetic acid and scavengers, crystalline phenol, thioanisole, ethanedithol and water for a period of 1.5 to 5.0 hours at room temperature to obtain 276 mg of the crude peptide. The crude peptide was analysed on a C, 18 analytical reverse phase HPLC column (250×4) on a gradient system comprising of acetonitrile and water in 0.1% TFA as described previously. The sugar amino acid, Saa3, used in the peptide sequence was racemic in nature and was resolved into two enantiomers, which appeared as two prominent peaks on HPLC. The individual peaks were purified on a preparative HPLC system using C, 18 Reverse Phase column in a gradient of 0.1% TFA in acetonitrile and water and lyophilized. The two pure enantiomers were sent for MALDI mass spectrometer analysis. The observed molecular weights for the two peptide enantiomers were 958.2 and 958.4 respectively and were in agreement with the calculated molecular weight of 957.

EXAMPLE 5

Leu-Met-Tyr-Saa4-Tyr-Leu-Lys (SEQ ID NO: 13)

The above peptide sequence was synthesized on Wang resin (Substitution=0.95 mM/g; Scale of synthesis=1 mM) in a similar way as described in the examples above to give 1.96 g of the peptide loaded resin. Cleavage of the peptide from the resin was carried out in a cleavage mixture consisting of trifluoroacetic acid and scavengers, crystalline phenol, thioanisole, ethanedithol and water for a period of 1.5 to 5.0 hours at room temperature to obtain 998 mg of the crude peptide. The peptide was purified on C-18 reverse phase column by HPLC and the single prominent peak was collected and lyophilized.

EXAMPLE 6

Met-Saa1-Tyr-Leu (SEQ ID NO: 14)

The above peptide sequence was synthesized on Wang resin in a similar way as described in the examples above. Sugar Amino Acid Saa1 was used. Synthesis was started on 1 mM scale (Substitution of Wang=0.95 mM/g) to obtain 1.42 g of peptide-loaded resin on completion of synthesis. The peptide was cleaved from the resin using crystalline phenol, thioanisole, ethanedithol and water for a period of 1.5 to 5.0 hours at room temperature to obtain 302 mg of the crude peptide as a single peak. On purification by RP-HPLC C-18 column, 203 mg of the purified peptide (>95% purity) was obtained.

EXAMPLE 7

Met-Saa3-Tyr-Leu (SEQ ID NO: 16)

The above peptide sequence was synthesized on Wang resin on 1.8 mM scale in a similar way as described in Example 1 to obtain 2.6 g of peptide loaded resin. Since the sugar amino acid, Saa3, used in the peptide sequence was racemic in nature, the peptide which was collected as a mixture of the two peaks (SEQ ID NO: 16), LC-MS analysis revealed correct molecular mass (calculated mass=552, observed mass=553).

EXAMPLE 8

Met-Saa4-Tyr-Leu (SEQ ID NO: 17)

The above peptide sequence is similar to the peptide in SEQ ID NO: 16, except that the chiral sugar amino acid Saa4(2R, 5S) has been used in place of amino acid Saa3.0.926 g of peptide loaded resin was obtained on 0.475 mM scale on Wang resin (Substitution=0.95 mM/g), which yielded 209 mg of the crude product on cleavage and 86 mg of the pure peptide of correct molecular mass (Expected mol. Mass=552; Observed mass=553.4) on HPLC purification.

EXAMPLE 9

Leu-Met-Saa4-Tyr-Leu-Lys (SEQ ID NO: 21)

The above peptide sequence was synthesized on 1 mM scale on Wang resin (Substitution=0.95 mM/g) to give 1.695 g of peptide-loaded resin on completion of synthesis. On cleavage from the resin using trifluoroacetic acid and scavengers, crystalline phenol, thioanisole, ethanedithol and water for a period of 1.5 to 5.0 hours at room temperature, 825 mg of the crude product was obtained. It was purified on C-18 RP-HPLC column to give pure peptide of correct molecular mass.

Conformational Studies of Synthesized Peptides using NMR

The incorporation of a carboxylic acid and an amino function into a cyclic carbohydrate skeleton results in conformationally restricted sugar amino acids (Schweizer, F; Angew. Chem. Int. Ed. (2002) 41: 230–253). The rigidity can be used to generate secondary structures when the sugar amino acids are oligomerized or incorporated into short peptides.

EXAMPLE 10

Met-Saa4-Tyr-Leu (SEQ ID NO: 17)

Solution conformation of the peptide Met-Saa4-Tyr-Leu-OH (SEQ ID NO: 17) was extensively studied in DMSO-$d_6$ by using various NMR experiments. As the Saa units are dipeptide isosteres, the sequence involving in the peptide Met-Saa4-Tyr-Leu is equivalent to a pentapeptide. Only tyrosine amide proton chemical shift has low magnitude of temperature coefficient ($\Delta\delta/\Delta T$=–2.8 ppb/° K) indicating its participation in intramolecular hydrogen bonding. The presence of ROESY cross peaks between TyrNH-SaaC2H, TyrNH-SaaC6H coupled with the tyrosine amide hydrogen bonding suggests that the observed hydrogen bond is between TyrNH→MetCO resulting in a 10-membered β-turn like structure, similar to that observed in several Saa oligomers (Fleet, G. W. J. etal: J. Chem. Soc., Perkin Trans. 1 2000, 3666–3679) and also in SEQ ID NO:2. Appearance of a rOe cross peak between the SaaC2H-SaaC5H indicates that the two protons are on the same side of the five membered ring. The $^3J_{NH—C\alpha H}$ for tyrosine and Leu residues at 8.3 and 7.9 Hz, respectively, indicate that the backbone φ angles show propensity of being in the β-region of the Ramachandran plot. The cross-peak intensities in the ROESY spectrum of SEQ ID NO:8 were used for obtaining the restraints in the MD calculations. The energy-minimized structures sampled during the MD simulation studies clearly show the hydrogen-bonded turn-structure of the compound.

EXAMPLE 11

A stock solution of the peptides listed in Examples 1 to 9 is prepared with a pH of approximately 3.5 to 7.0 but preferably 4.0 to 5.5. Although sterile phosphate buffered saline was used to prepare each stock solution for the testing described in the following example, other diluents may be used such as buffered saline, isotonic NaCl, Ringer's solution, water, distilled water, polyethylene glycol (neat or in water), Tween in water, dimethylsulfoxide up to 50% in water, propylene glycol (neat or in water), phosphate buffered saline, balanced salt solution, glycerol, and other conventional fluids that are suitable for parentral administration. To obtain a pH in the range of approximately 3.5 to 7.0, for each stock solution, the pH can be adjusted by using 1N HCl for lowering the pH or 1N NaOH for raising the pH, although other buffers such as citrate buffer, phosphate buffer and the like or other conventional agents for adjusting the pH can be used. The stock solution of each peptide is then mixed in appropriate dilutions so as to give a final concentration of $10^{-6}$ M to $10^{-10}$ M, but more preferably in the range of $10^{-8}$ to $10^{-9}$ M. Stock solution for the pharmaceutically acceptable salts is prepared in the same way.

Formulation of A Dose of The Combination For Parenteral Administration

A dose of the formulation of peptides listed in Examples 1 to 9 was prepared in the following way. A stock solution of each of the peptides was first prepared using sterile phosphate buffered saline with an approximate pH of 4.0 to 5.5. The total weight of a single dose is between 1 to 200 mg. This conforms to a dose of 10–400 μg/Kg. B. Wt. body weight of the mammal. These peptides have their best in vitro or systemic biological activity (anticancer) when their individual concentrations range between $10^{-6}$ M to $10^{-10}$ M (preferably $10^{-8}$ M to $10^{-9}$ M). To achieve therapeutically effective systemic concentrations, a dose of 10–400 μg/Kg. B. Wt of the mammal needs to be administered.

EXAMPLE 12

In Vitro Cytotoxicity of Synthesized Peptide Analogs

The cytotoxic effect of the peptides listed in the Examples 1 to 9 above was studied by MTT assay. The MTT assay is based on the principle of uptake of MTT [3-[4,5-dimethylthiazol-2-yl]-2,5-diphenyl tetrazolium bromide], a tetrazolium salt, by the metabolically active cells where it is metabolized by active mitochondria into a blue colored formazan product which can be read spectrophotometrically. Briefly, tumor cells of ovary, colon, larynx, pancreas, oral cavity, liver and endothelial cells were incubated with the peptide analogs at a concentration of $10^{-6}$ to $10^{-9}$ M for 48 hours at 37° C. in a 96-well culture plate, followed by the addition of 100 μg MTT and further incubation of 1 hour. The formazan crystals formed inside the cells were dissolved with a detergent comprising of 10% Sodium dodecyl sulfate and 0.01 N HCl and optical density read on a multi-scan ELISA reader. The optical density was directly proportional to the number of proliferating and metabolically active cells. Percent cytotoxicity of peptide analogs is shown in the following Tables. The following cell lines were used. PA1(human ovary), PTC (colon), HeP-2 (larynx), MiaPaCa.2 (human pancreas), KB (oral), ECV-304 (endothelial) and HeP-G2 (liver).

Percent Cytotoxicity of SEQ ID NO: 3 on various human tumor cell lines

| Cell lines | Concentration of peptide | | | |
|---|---|---|---|---|
| | 1 nM | 10 nM | 100 nM | 1 μM |
| PA1 | 16.8 ± 1.4 | 18.0 ± 1.8 | 12.5 ± 0.0 | 10.8 ± 0.6 |
| PTC | NA | NA | NA | NA |
| HeP-2 | 12.6 ± 2.8 | 15.4 ± 1.3 | 13.9 ± 0.5 | 10.8 ± 0.5 |
| MiaPaCa.2 | 21.8 ± 2.1 | 24.0 ± 2.7 | 17.9 ± 1.8 | 13.9 ± 0.4 |
| KB | 12.9 ± 1.3 | 17.7 ± 0.5 | 14.9 ± 1.1 | 9.5 ± 0.1 |
| ECV-304 | ND | ND | ND | ND |
| HeP-G2 | 12.3 ± 0.4 | 10.7 ± 0.1 | 9.5 ± 1.0 | 6.9 ± 0.0 |

NA = Not Active;
ND = Not Done

Percent Cytotoxicity of SEQ ID NO: 8 on human tumor cell lines

| Cell lines | Concentration of peptide | | | |
|---|---|---|---|---|
| | 1 nM | 10 nM | 100 nM | 1 μM |
| PA1 | 12.7 ± 1.9 | 18.0 ± 1.0 | 14.8 ± 1.9 | 9.6 ± 1.0 |
| PTC | NA | NA | NA | NA |
| HeP-2 | NA | NA | NA | NA |
| MiaPaCa.2 | 22.9 ± 2.2 | 25.5 ± 2.9 | 22.9 ± 2.6 | 19.0 ± 0.6 |
| KB | NA | NA | NA | NA |
| ECV-304 | 15.3 ± 1.6 | 12.7 ± 1.6 | 10.8 ± 2.9 | 7.9 ± 0.1 |
| HeP-G2 | NA | NA | NA | NA |

NA = Not Active

Percent Cytotoxicity of SEQ ID NO: 9 on various human tumor cell lines

| Cell lines | Concentration of peptide | | | |
|---|---|---|---|---|
| | 1 nM | 10 nM | 100 nM | 1 μM |
| PA1 | 21.9 ± 2.2 | 22.7 ± 2.1 | 26.5 ± 2.5 | 22.1 ± 2.9 |
| PTC | 33.5 ± 2.9 | 31.9 ± 2.8 | 29.5 ± 2.7 | 26.0 ± 2.2 |
| HeP-2 | 20.9 ± 2.0 | 21.0 ± 1.9 | 18.8 ± 1.9 | 14.6 ± 1.6 |
| MiaPaCa.2 | 14.8 ± 2.9 | 12.9 ± 1.5 | 9.3 ± 1.1 | 5.9 ± 0.0 |
| KB | 14.5 ± 1.8 | 12.5 ± 1.9 | 10.5 ± 1.2 | NA |
| ECV-304 | 12.8 ± 1.4 | 15.8 ± 1.1 | 10.4 ± 2.0 | 7.9 ± 0.4 |
| HeP-G2 | 11.2 ± 1.1 | 10.7 ± 1.1 | NA | NA |

NA = Not Active

Percent Cytotoxicity of SEQ ID NO: 10 on various human tumor cell lines

| Cell lines | Concentration of peptide | | | |
|---|---|---|---|---|
| | 1 nM | 10 nM | 100 nM | 1 μM |
| PA1 | 37.5 ± 3.8 | 32.0 ± 2.9 | 31.0 ± 2.7 | 28.4 ± 2.2 |
| PTC | 30.5 ± 3.2 | 28.0 ± 2.2 | 25.6 ± 2.2 | 21.8 ± 2.8 |
| HeP-2 | 35.4 ± 2.9 | 32.0 ± 2.1 | 31.8 ± 3.1 | 28.9 ± 2.1 |
| MiaPaCa.2 | 14.9 ± 1.9 | 12.0 ± 1.7 | 9.0 ± 0.6 | NA |
| KB | 32.0 ± 2.5 | 31.9 ± 2.9 | 29.6 ± 0.7 | 26.0 ± 1.8 |
| ECV-304 | 15.2 ± 1.0 | 12.9 ± 0.5 | 9.4 ± 0.2 | NA |
| HeP-G2 | NA | NA | NA | NA |

NA = Not Active

Percent Cytotoxicity of SEQ ID NO: 12

| Cell lines | Concentration of peptide | | | |
|---|---|---|---|---|
| | 1 nM | 10 nM | 100 nM | 1 μM |
| PA1 | 20.2 ± 2.1 | 24.6 ± 2.7 | 39.3 ± 3.0 | 32.1 ± 2.0 |
| PTC | 12.7 ± 1.8 | 14.8 ± 1.9 | 10.8 ± 2.0 | NA |
| HeP-2 | 21.9 ± 2.9 | 39.3 ± 3.2 | 32.2 ± 1.9 | 28.9 ± 3.2 |
| MiaPaCa.2 | 23.8 ± 3.2 | 30.6 ± 3.9 | 21.9 ± 0.2 | 13.9 ± 2.7 |
| KB | 32.9 ± 4.3 | 37.4 ± 2.9 | 33.2 ± 0.4 | 19.9 ± 1.9 |
| ECV-304 | 32.0 ± 3.9 | 36.9 ± 3.2 | 27.9 ± 2.9 | 22.2 ± 2.2 |
| HeP-G2 | NA | NA | NA | NA |

NA = Not Active

Percent Cytotoxicity of SEQ ID NO: 13 on various human tumor cell lines

| Cell lines | Concentration of peptide | | | |
|---|---|---|---|---|
| | 1 nM | 10 nM | 100 nM | 1 μM |
| PA1 | 44.0 ± 3.9 | 41.0 ± 4.2 | 38.0 ± 3.9 | 35.5 ± 2.4 |
| PTC | 28.5 ± 2.0 | 26.0 ± 2.9 | 22.8 ± 2.1 | 20.8 ± 1.8 |
| HeP-2 | 23.0 ± 2.1 | 21.8 ± 1.8 | 17.9 ± 1.9 | 16.4 ± 0.6 |
| MiaPaCa.2 | 17.5 ± 1.9 | 14.0 ± 0.6 | 8.0 ± 0.6 | NA |
| KB | 30.0 ± 2.8 | 27.9 ± 2.1 | 26.9 ± 2.1 | 21.4 ± 2.1 |
| ECV-304 | 23.0 ± 1.6 | 21.0 ± 2.6 | 18.0 ± 1.6 | 12.1 ± 1.3 |
| HeP-G2 | NA | NA | NA | NA |

NA = Not Active

Percent Cytotoxicity of SEQ ID NO: 14 on various human tumor cell lines

| Cell lines | Concentration of peptide | | | |
|---|---|---|---|---|
| | 1 nM | 10 nM | 100 nM | 1 μM |
| PA1 | 35.9 ± 3.7 | 32.1 ± 2.2 | 28.0 ± 2.2 | 21.5 ± 2.1 |
| PTC | 28.9 ± 2.2 | 26.9 ± 2.9 | 21.8 ± 1.0 | 15.0 ± 0.5 |
| HeP-2 | 11.0 ± 1.9 | 10.6 ± 1.1 | 6.0 ± 0.8 | NA |
| MiaPaCa.2 | 17.0 ± 1.7 | 13.9 ± 1.1 | 7.0 ± 0.3 | NA |
| KB | 14.5 ± 0.4 | 12.9 ± 0.5 | NA | NA |
| ECV-304 | 12.7 ± 0.4 | 13.0 ± 0.6 | 6.0 ± 0.0 | NA |
| HeP-G2 | NA | NA | NA | NA |

NA = Not Active

Percent Cytotoxicity of SEQ ID NO: 16 on various human tumor cell lines

| Cell lines | Concentration of peptide | | | |
|---|---|---|---|---|
| | 1 nM | 10 nM | 100 nM | 1 μM |
| PA1 | 24.0 ± 2.1 | 22.9 ± 2.1 | 19.0 ± 1.0 | 16.8 ± 1.8 |
| PTC | NA | NA | NA | NA |
| HeP-2 | 16.5 ± 1.6 | 19.2 ± 1.6 | 12.6 ± 0.5 | 10.9 ± 1.1 |
| MiaPaCa.2 | NA | NA | NA | NA |
| KB | 9.3 ± 0.3 | 9.7 ± 0.4 | 3.2 ± 0.1 | NA |
| ECV-304 | 9.3 ± 0.6 | 7.9 ± 0.1 | NA | NA |
| HeP-G2 | 11.0 ± 1.1 | 12.8 ± 0.7 | 11.4 ± 0.7 | 9.8 ± 0.7 |

NA = Not Active

Percent Cytotoxicity of SEQ ID NO: 17 on various human tumor cell lines

| Cell lines | Concentration of peptide | | | |
|---|---|---|---|---|
| | 1 nM | 10 nM | 100 nM | 1 μM |
| PA1 | 18.2 ± 1.1 | 17.8 ± 1.7 | 15.9 ± 0.6 | 6.0 ± 0.7 |
| PTC | 12.0 ± 1.7 | 11.9 ± 1.4 | 10.4 ± 0.6 | 8.4 ± 1.0 |
| HeP-2 | 33.6 ± 2.7 | 31.7 ± 3.2 | 29.0 ± 0.4 | 27.9 ± 2.9 |
| MiaPaCa.2 | 23.0 ± 2.1 | 21.8 ± 1.9 | 17.0 ± 0.9 | 16.0 ± 1.4 |
| KB | 24.9 ± 2.7 | 21.9 ± 2.0 | 20.5 ± 2.1 | 17.9 ± 0.6 |
| ECV-304 | 16.4 ± 1.9 | 13.9 ± 0.5 | 11.9 ± 1.1 | NA |
| HeP-G2 | 12.8 ± 0.6 | 17.9 ± 1.4 | 20.9 ± 1.4 | 12.0 ± 0.7 |

NA = Not Active

Percent Cytotoxicity of SEQ ID NO: 18 on various human tumor cell lines

| Cell lines | Concentration of peptide | | | |
|---|---|---|---|---|
| | 1 nM | 10 nM | 100 nM | 1 μM |
| PA1 | 18.3 ± 1.8 | 22.8 ± 2.9 | 21.8 ± 2.1 | 20.3 ± 2.6 |
| PTC | 19.0 ± 1.6 | 28.4 ± 1.0 | 23.9 ± 2.9 | 21.7 ± 1.5 |
| HeP-2 | 47.0 ± 4.8 | 38.3 ± 2.0 | 35.8 ± 2.4 | 32.9 ± 2.6 |
| MiaPaCa.2 | 24.8 ± 2.0 | 21.0 ± 2.6 | 18.5 ± 0.6 | 15.0 ± 0.6 |
| KB | 15.9 ± 1.0 | 12.0 ± 0.3 | 14.0 ± 1.0 | 9.3 ± 0.4 |
| ECV-304 | 11.0 ± 0.6 | NA | NA | NA |
| HeP-G2 | NA | NA | NA | NA |

NA = Not Active

A PubMed search of the National Library of Medicine was carried out to determine the relevance of cell lines used by us for determining the anticancer activity of the peptides. While HT29 (human colon) showed 2021 "hits" when searched with reference to cancer, other human cancer cell lines used by us also showed large number of hits: 269 for HeP-2, 449 for ECV-304, 1276 for HeP-G2 and 182 for PA-1. This clearly shows the extensive use of these cell lines in cancer research. Further, it is a common and standard practice and norm for testing molecules for anticancer activity in vitro on human tumor cell lines. (Br. J. Cancer. 2001 May 18; 84(10): 1289–90 (Flasks, Fibres and Flanks—Preclinical tumor models for predicting clinical antitumor activity). The authors of this article report that in vitro activity against 6 or more lung or breast cancer cell lines does predict xenograft activity against these tumor types. In articles "Semin. Oncol. 1992 December; 19(6): 622–38 (The National Cancer Institute: cancer drug discovery and development program) and "Jpn. J. Antibiot. 1977 December; 30 Suppl:35–40 (Antitumor screening procedures of the National Cancer Institute)" extensive use of human tumor cell lines for identification of potential cytotoxic drugs is described.

EXAMPLE 13

In Vivo Antitumour Activity of the Novel Synthesized Peptide Analogs on Primary Tumor (Colon) Xenografted Mice The antitumor activity of the peptide (SEQ ID NO: 12) was studied in human colon adenocarcinoma (PTC) xenografts in nude mice. PTC tumor xenografts were grown in Balb/c athymic mice by subcutaneous inoculation of a single cell suspension of PTC cells ($15 \times 10^6$ cells/100 μL). The tumor bearing animals were divided into 2 groups of five animals each including one group comprising untreated control animals. Treatment with novel peptide was initiated when the average tumor volumes, as measured using a vernier caliper, were between 400–800 mm$^3$. Solution of SEQ ID NO 12 was prepared at a concentration of 100 μg/ml and intravenously administered to the assigned group of tumor bearing animals at a dose of 0.5 mg/Kg. B. Wt twice a day so that the total dose of 1 mg/Kg. B. Wt was administered to each animal. The treatment was continued for a period of 21 days.

Figure 1:
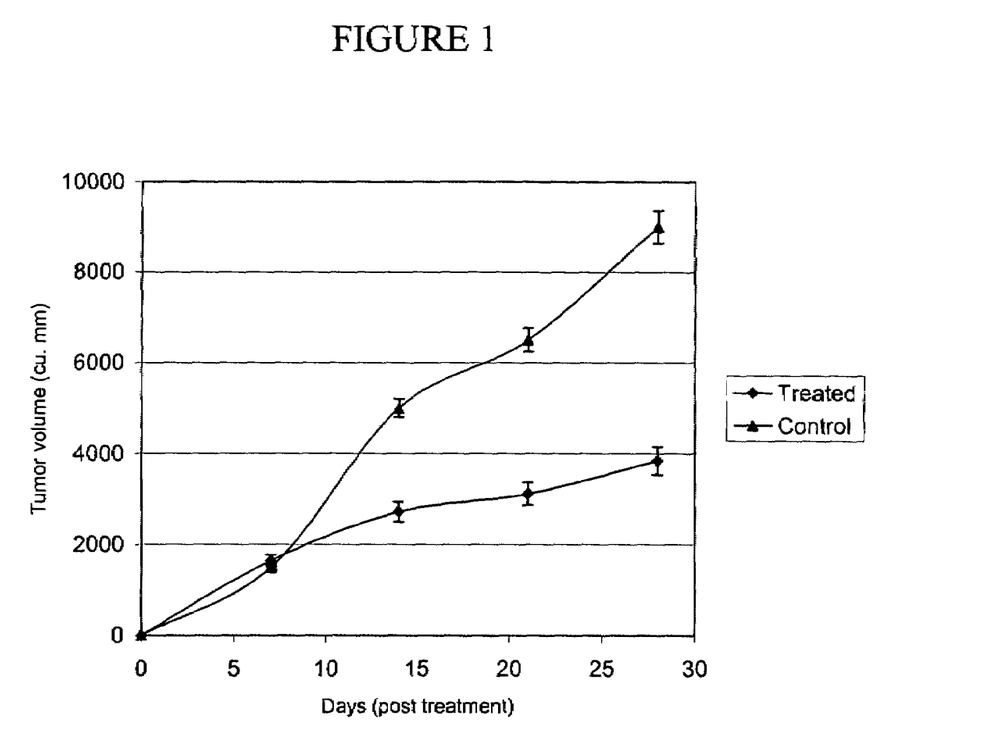
FIG. 1 shows the tumor volume of treated and untreated animals.

The antitumor activity of the compounds was monitored by measuring tumor volumes every fourth day using the formula W*W*L*0.4 (W=smaller diameter, L=larger diameter). The percentage inhibition of tumor growth was calculated using the formula (1-tumor volume-treated/tumor volume-control)* 100. FIG. 1 shows the tumor tumor volume kinetics till day 21 in the treated and untreated animals. Novel peptide SEQ ID NO: 12 (NDR3b) showed a significant antitumor activity on PTC xenografts. The percentage inhibition of tumor growth caused by the peptide (SEQ ID NO: 12) as compared to controls on day 21 was 57.2%.

What is claimed is:

1. A peptide of the formula X-Met-A1-A2-A3-Tyr-Leu-Y or a pharmaceutically acceptable salt thereof, wherein X is Leu or deleted, Y is Lys or deleted, A1 is Tyr, A2 is Pro and A3 is Thr or A1-A2-A3 together, A1-A2 together, A2-A3 together or A2 is a furanoid sugar amino acid selected from the group consisting of Saa-1, Saa-3 and Saa-4 wherein at least one of A1-A2-A3, A1-A2, A2-A3 or A2 is Saa-1, Saa-3 or Saa-4, wherein Saa-1, Saa-3, and Saa-4 are represented by the structure where, when the pentacyclic ring is aromatic the sugar is Saa-1, where position 2 carboxylic acid has a S configuration and position 5 amino methyl group has R configuration the sugar is Saa-4 and where both the Position 2 carboxylic acid and position 5 amino methyl group have achiral configuration the sugar is Saa-3.

2. The peptide of claim 1 selected from the group consisting of:

Leu-Met-Tyr-Saa1-Thr-Tyr-Leu-Lys    (SEQ ID NO: 2)

Leu-Met-Tyr-Saa3-Thr-Tyr-Leu-Lys    (SEQ ID NO: 4)

Leu-Met-Tyr-Saa4-Thr-Tyr-Leu-Lys    (SEQ ID NO: 5)

Leu-Met-Saa1-Thr-Tyr-Leu-Lys        (SEQ ID NO: 6)

Leu-Met-Saa3-Thr-Tyr-Leu-Lys        (SEQ ID NO: 8)

Leu-Met-Saa4-Thr-Tyr-Leu-Lys        (SEQ ID NO: 9)

Leu-Met-Tyr-Saa1-Tyr-Leu-Lys        (SEQ ID NO: 10)

```
Leu-Met-Tyr-Saa3-Tyr-Leu-Lys    (SEQ ID NO: 12)

Leu-Met-Tyr-Saa4-Tyr-Leu-Lys    (SEQ ID NO: 13)

Met-Saa1-Tyr-Leu                (SEQ ID NO: 14)

Met-Saa3-Tyr-Leu                (SEQ ID NO: 16)

Met-Saa4-Tyr-Leu                (SEQ ID NO: 17)

Leu-Met-Saa1-Tyr-Leu-Lys        (SEQ ID NO: 18)

Leu-Met-Saa3-Tyr-Leu-Lys        (SEQ ID NO: 20)
                                and Leu-Met-Saa4-Tyr-Leu-Lys        (SEQ ID NO: 21).
```

3. A peptide according to claim 1, wherein the pharmaceutically acceptable salt is selected from the group consisting of acetate, ascorbate, benzoate, citrate, oxalate, stearate, trifluoroacetate, succinates, tartarate, lactate, fumarate, gluconate, glutamate, phosphate/diphosphate, valerate, Ca, Li, Mg, Na, K; salts of amino acids selected from the group consisting of lysine and arginine; guanidine, ammonium, substituted ammonium salts and aluminum salts.

4. A composition comprising a peptide as claimed in claim 1 and a carrier, excipient, diluent or solvent.

5. A composition comprising a peptide as claimed in claim 2 and a pharmaceutically acceptable carrier, excipient, diluent or solvent.

6. A composition comprising a peptide as claimed in claim 3 and a carrier, excipient, diluent or solvent.

7. The composition as claimed in claim 4, wherein the concentration of each peptide is about $10^{-6}$ M to $10^{-10}$ M.

8. The composition as claimed in claim 5, wherein the concentration of each peptide is about $10^{-6}$ M to $10^{-10}$ M.

9. The composition as claimed in claim 6, wherein the concentration of each peptide is about $10^{-6}$ M to $10^{-10}$ M.

10. The composition as claimed in claim 4, wherein the weight of the peptides in a single dose is between 1 to 20 mg.

11. The composition as claimed in claim 5, wherein the weight of the peptides in a single dose is between 1 to 20 mg.

12. The composition as claimed in claim 6, wherein the weight of the peptides in a single dose is between 1 to 20 mg.

13. The pharmaceutical composition according to claim 4, wherein a single dose is 10–400 ug of peptides/Kg of body weight.

14. The pharmaceutical composition according to claim 5, wherein a single dose is 10–400 ug of peptides/Kg of body weight.

15. The pharmaceutical composition according to claim 6, wherein a single dose is 10–400 ug of peptides/Kg of body weight.

16. A method of killing or inhibiting the multiplication of tumor cells or cancer cells in a human or other animal, the method comprising administering to the human or animal an effective amount of a peptide as claimed in claim 1 or a pharmaceutically acceptable salt thereof.

17. A method of killing or inhibiting the multiplication of tumor cells or cancer cells in a human or other animal, the method comprising administering to the human or animal an effective amount of a peptide as claimed in claim 2 or a pharmaceutically acceptable salt thereof.

18. A method of killing or inhibiting the multiplication of tumor cells or cancer cells in a human or other animal, the method comprising administering to the human or animal an effective amount of a peptide as claimed in claim 3 or a pharmaceutically acceptable salt thereof.

19. A method for treating cancer comprising administering to a human or animal in need thereof comprising administering to the human or animal a therapeutically effective amount of a peptide as claimed in claim 1 or a pharmaceutically acceptable salt thereof.

20. The method according to claim 19, wherein the cancer is selected from the group consisting of cancer of the ovary, colon, larynx, pancreas, oral cavity, liver and endothelial cells.

21. A method for treating cancer comprising administering to a human or animal in need thereof comprising administering to the human or animal a therapeutically effective amount of a peptide as claimed in claim 2 or a pharmaceutically acceptable salt thereof.

22. The method according to claim 21, wherein the cancer is selected from the group consisting of cancer of the ovary, colon, larynx, pancreas, oral cavity, liver and endothelial cells.

23. A method for treating cancer comprising administering to a human or animal in need thereof comprising administering to the human or animal a therapeutically effective amount of a peptide as claimed in claim 3 or a pharmaceutically acceptable salt thereof.

24. The method according to claim 23, wherein the cancer is selected from the group consisting of cancer of the ovary, colon, larynx, pancreas, oral cavity, liver and endothelial cells.

* * * * *

```
                         SEQUENCE LISTING

<160> NUMBER OF SEQ ID NOS: 21

<210> SEQ ID NO 1
<211> LENGTH: 8
<212> TYPE: PRT
<213> ORGANISM: Artificial
<220> FEATURE:
<223> OTHER INFORMATION: This peptide was synthetically generated.

<400> SEQUENCE: 1

Leu Met Tyr Pro Thr Tyr Leu Lys
1               5

<210> SEQ ID NO 2
<211> LENGTH: 8
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (4)..(4)
<223> OTHER INFORMATION: Saa1 = Furanoid Sugar Amino Acid

<400> SEQUENCE: 2

Leu Met Tyr Xaa Thr Tyr Leu Lys
1               5

<210> SEQ ID NO 3
<211> LENGTH: 8
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (4)..(4)
<223> OTHER INFORMATION: Saa2 = Furanoid Sugar Amino Acid

<400> SEQUENCE: 3

Leu Met Tyr Xaa Thr Tyr Leu Lys
1               5

<210> SEQ ID NO 4
<211> LENGTH: 8
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (4)..(4)
<223> OTHER INFORMATION: Saa3 = Furanoid Sugar Amino Acid

<400> SEQUENCE: 4

Leu Met Tyr Xaa Thr Tyr Leu Lys
1               5

<210> SEQ ID NO 5
<211> LENGTH: 8
<212> TYPE: PRT
<213> ORGANISM: Artificial
<220> FEATURE:
```

<223> OTHER INFORMATION: This peptide was synthetically generated.
<220> FEATURE:
<221> NAME/KEY: MISC_FEATURE
<222> LOCATION: (4)..(4)
<223> OTHER INFORMATION: Saa4 = Furanoid Sugar Amino Acid

<400> SEQUENCE: 5

Leu Met Tyr Xaa Thr Tyr Leu Lys
1               5

<210> SEQ ID NO 6
<211> LENGTH: 7
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (3)..(3)
<223> OTHER INFORMATION: Saa1 = Furanoid Sugar Amino Acid

<400> SEQUENCE: 6

Leu Met Xaa Thr Tyr Leu Lys
1               5

<210> SEQ ID NO 7
<211> LENGTH: 7
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (3)..(3)
<223> OTHER INFORMATION: Saa2 = Furanoid Sugar Amino Acids

<400> SEQUENCE: 7

Leu Met Xaa Thr Tyr Leu Lys
1               5

<210> SEQ ID NO 8
<211> LENGTH: 7
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (3)..(3)
<223> OTHER INFORMATION: Saa3 = Furanoid Sugar Amino Acids

<400> SEQUENCE: 8

Leu Met Xaa Thr Tyr Leu Lys
1               5

<210> SEQ ID NO 9
<211> LENGTH: 7
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (3)..(3)
<223> OTHER INFORMATION: Saa4 = Furanoid Sugar Amino Acids

<400> SEQUENCE: 9

Leu Met Xaa Thr Tyr Leu Lys
1               5

```
<210> SEQ ID NO 10
<211> LENGTH: 7
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (4)..(4)
<223> OTHER INFORMATION: Saa1 = Furanoid Sugar Amino Acids

<400> SEQUENCE: 10

Leu Met Tyr Xaa Tyr Leu Lys
1               5

<210> SEQ ID NO 11
<211> LENGTH: 7
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (4)..(4)
<223> OTHER INFORMATION: Saa2 = Furanoid Sugar Amino Acids

<400> SEQUENCE: 11

Leu Met Tyr Xaa Tyr Leu Lys
1               5

<210> SEQ ID NO 12
<211> LENGTH: 7
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (4)..(4)
<223> OTHER INFORMATION: Saa3 = Furanoid Sugar Amino Acid

<400> SEQUENCE: 12

Leu Met Tyr Xaa Tyr Leu Lys
1               5

<210> SEQ ID NO 13
<211> LENGTH: 7
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (4)..(4)
<223> OTHER INFORMATION: Saa4 = Furanoid Sugar Amino Acid

<400> SEQUENCE: 13

Leu Met Tyr Xaa Tyr Leu Lys
1               5

<210> SEQ ID NO 14
<211> LENGTH: 4
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (2)..(2)
<223> OTHER INFORMATION: Saa1 = Furanoid Sugar Amino Acids
```

```
<400> SEQUENCE: 14

Met Xaa Tyr Leu
1

<210> SEQ ID NO 15
<211> LENGTH: 4
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (2)..(2)
<223> OTHER INFORMATION: Saa2 = Furanoid Sugar Amino Acid

<400> SEQUENCE: 15

Met Xaa Tyr Leu
1

<210> SEQ ID NO 16
<211> LENGTH: 4
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (2)..(2)
<223> OTHER INFORMATION: Saa3 = Furanoid Sugar Amino Acids
<220> FEATURE:
<221> NAME/KEY: MISC_FEATURE
<222> LOCATION: (2)..(2)
<223> OTHER INFORMATION: Saa3 = Furanoid Sugar Amino Acid

<400> SEQUENCE: 16

Met Xaa Tyr Leu
1

<210> SEQ ID NO 17
<211> LENGTH: 4
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (2)..(2)
<223> OTHER INFORMATION: Saa4 = Furanoid Sugar Amino Acid

<400> SEQUENCE: 17

Met Xaa Tyr Leu
1

<210> SEQ ID NO 18
<211> LENGTH: 6
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (3)..(3)
<223> OTHER INFORMATION: Saa1 = Furanoid Sugar Amino Acid

<400> SEQUENCE: 18

Leu Met Xaa Tyr Leu Lys
1               5
```

```
<210> SEQ ID NO 19
<211> LENGTH: 6
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (3)..(3)
<223> OTHER INFORMATION: Saa2 = Furanoid Sugar Amino Acid

<400> SEQUENCE: 19

Leu Met Xaa Tyr Leu Lys
1               5

<210> SEQ ID NO 20
<211> LENGTH: 6
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (3)..(3)
<223> OTHER INFORMATION: Saa3 = Furanoid Sugar Amino Acid

<400> SEQUENCE: 20

Leu Met Xaa Tyr Leu Lys
1               5

<210> SEQ ID NO 21
<211> LENGTH: 6
<212> TYPE: PRT
<213> ORGANISM: Artificial
<220> FEATURE:
<223> OTHER INFORMATION: This peptide was synthetically generated.
<220> FEATURE:
<221> NAME/KEY: MISC_FEATURE
<222> LOCATION: (3)..(3)
<223> OTHER INFORMATION: Saa4 = Furanoid Sugar Amino Acid

<400> SEQUENCE: 21

Leu Met Xaa Tyr Leu Lys
1               5
```